(12) United States Patent
Knight

(10) Patent No.: US 11,779,748 B2
(45) Date of Patent: Oct. 10, 2023

(54) MEDICAL COILED TUBING

(71) Applicant: Codan US Corporation, Santa Ana, CA (US)

(72) Inventor: Thomas F. Knight, Santa Ana, CA (US)

(73) Assignee: CODAN US CORPORATION, Santa Ana, CA (US)

(*) Notice: Subject to any disclaimer, the term of this patent is extended or adjusted under 35 U.S.C. 154(b) by 393 days.

(21) Appl. No.: 17/037,387

(22) Filed: Sep. 29, 2020

(65) Prior Publication Data

US 2022/0096813 A1    Mar. 31, 2022

(51) Int. Cl.
*A61M 39/18* (2006.01)
*A61L 2/20* (2006.01)
*A61M 39/08* (2006.01)

(52) U.S. Cl.
CPC .............. *A61M 39/18* (2013.01); *A61L 2/206* (2013.01); *A61L 2202/24* (2013.01); *A61M 39/08* (2013.01); *A61M 2039/087* (2013.01); *A61M 2205/02* (2013.01); *A61M 2207/10* (2013.01)

(58) Field of Classification Search
CPC .... A61L 2/206; A61L 29/041; A61L 2202/24; A61M 25/00; A61M 25/002; A61M 25/0009; A61M 39/08; A61M 39/18; A61M 2039/087; A61M 2205/02; A61M 2207/10; B29L 2031/7542; B29C 53/12; B29C 53/36; B29C 53/083; B29K 2027/06
See application file for complete search history.

(56) References Cited

U.S. PATENT DOCUMENTS

| | | | | |
|---|---|---|---|---|
| 3,910,808 A | * | 10/1975 | Steward | ............... B29C 53/78 156/429 |
| 4,260,143 A | * | 4/1981 | Kliger | ............... B29C 53/12 267/148 |
| 4,276,333 A | * | 6/1981 | Cobean | ............ A61M 25/0012 428/371 |
| 4,990,143 A | | 2/1991 | Sheridan | |

(Continued)

FOREIGN PATENT DOCUMENTS

| EP | 1557257 A1 | 7/2005 |
|---|---|---|
| WO | 9304722 A2 | 3/1993 |

OTHER PUBLICATIONS

V. K. Stokes, "Joing Methods for Plastics Composites: An Overview", Oct. 1989, Polymer Engineering and Science, vol. 29, No. 19, pp. 1313 (Year: 1989).*

(Continued)

*Primary Examiner* — Jennifer Wecker
*Assistant Examiner* — Brad C Pilsbury
(74) *Attorney, Agent, or Firm* — Kutak Rock LLP

(57) ABSTRACT

Disclosed herein are sterilized medical coiled tubing and process for producing the same. One process comprises: helically winding a length of the medical tubing along a mandrel such that adjacent turns of the medical tubing are in contact with each other; applying solvent where the turns of the medical tubing contact each other to produce coiled medical tubing; allowing the solvent to dry; removing the medical tubing from the mandrel after the solvent has dried; and subjecting the medical tubing to a sterilization process using ethylene oxide with in-chamber aeration.

14 Claims, 9 Drawing Sheets

(56) References Cited

U.S. PATENT DOCUMENTS

| | | | |
|---|---|---|---|
| 5,958,167 A * | 9/1999 | Van Driel | B29C 65/04 |
| | | | 264/491 |
| 6,258,195 B1 | 7/2001 | Holman | |
| 6,429,242 B1 * | 8/2002 | Macher | C09K 3/30 |
| | | | 524/113 |
| 6,735,491 B2 | 5/2004 | Byun | |
| 10,200,244 B2 * | 2/2019 | Kim | H04L 43/062 |
| 2005/0165366 A1 | 7/2005 | Brustad | |
| 2006/0021298 A1 * | 2/2006 | Van Caeneghem | B65B 1/02 |
| | | | 53/558 |
| 2006/0278547 A1 | 12/2006 | Rowe | |
| 2009/0318887 A1 * | 12/2009 | Sacchetti | A61M 39/08 |
| | | | 242/472.5 |
| 2016/0347492 A1 * | 12/2016 | Lu | A61L 2/07 |
| 2017/0348715 A1 * | 12/2017 | Beer | B05B 11/048 |
| 2019/0002176 A1 | 1/2019 | Proulx | |
| 2020/0102130 A1 * | 4/2020 | Parekh | B65D 1/0215 |

OTHER PUBLICATIONS

European Search Report in EP Patent Application No. 21199101.3, dated Jan. 18, 2022.

* cited by examiner

MEDICAL COILED TUBING

DESCRIPTION OF RELATED ART

The disclosed technology relates generally to medical devices, and more particularly, some embodiments relate to systems and methods for such devices.

SUMMARY

In general, one aspect disclosed features a process for producing a sterilized medical tubing coil, comprising: helically winding a length of the medical tubing along a mandrel such that adjacent turns of the medical tubing are in contact with each other; applying solvent where the turns of the medical tubing contact each other to produce coiled medical tubing; allowing the solvent to dry; removing the medical tubing from the mandrel after the solvent has dried; and subjecting the medical tubing to a sterilization process using ethylene oxide with in-chamber aeration.

Embodiments of the process may include one or more of the following features. In some embodiments, the solvent is cyclohexanone. In some embodiments, the mandrel is formed of polyoxymethylene. In some embodiments, the tubing is non-DEHP PVC or DEHP-free PVC. In some embodiments, applying solvent where the turns of the medical tubing contact each other comprises: applying solvent at multiple points between each pair of adjacent turns of the medical tubing. In some embodiments, applying the solvent where the coils of the medical tubing contact each other comprises: dipping a pin into a container of the solvent such that the solvent adheres to the pin; disposing the pin between where the coils of the medical tubing contact each other; and removing the pin from the coils of the medical tubing. In some embodiments, the pin is metal. In some embodiments, applying the solvent where the turns of the medical tubing contact each other comprises: dipping a comb comprising a plurality of parallel pins into a container of the solvent such that the solvent adheres to the pins; disposing each of the pins between respective turns of the medical tubing where the turns of the medical tubing contact each other; and removing the pins from the turns of the medical tubing. Some embodiments comprise cooling the mandrel before removing the medical tubing from the mandrel. In some embodiments, a surface of the mandrel contacted by the turns of the medical tubing is smooth. In some embodiments, a surface of the mandrel contacted by the turns of the medical tubing has a helical groove to receive the medical tubing. In some embodiments, removing the medical tubing from the mandrel comprises: rotating the mandrel and the medical tubing in opposite directions. Some embodiments comprise placing the coiled medical tubing in a synthetic container after removing the coiled medical tubing from the mandrel, and prior to subjecting the coiled medical tubing to the ethylene oxide sterilization process with in-chamber aeration. In some embodiments, the synthetic container is made of flashspun high-density polyethylene fibers.

In general, one aspect disclosed features an apparatus for producing a medical tubing coil, comprising: a mandrel configured to helically wind a length of the medical tubing along the mandrel such that adjacent turns of the medical tubing are in contact with each other; and a pin configured to apply solvent where the turns of the medical tubing contact each other to produce coiled medical tubing; wherein the solvent is allowed to dry before removing the medical tubing from the mandrel; and wherein the coiled medical tubing is subjected to a sterilization process using ethylene oxide with in-chamber aeration.

Embodiments of the apparatus may include one or more of the following features. In some embodiments, the solvent is cyclohexanone. In some embodiments, the pin is further configured to apply the solvent at multiple points between each pair of adjacent turns of the medical tubing.

In general, one aspect disclosed features a product made by a process comprising: helically winding a length of medical tubing along a mandrel such that adjacent turns of the medical tubing are in contact with each other; applying solvent where the turns of the medical tubing contact each other to produce coiled medical tubing; allowing the solvent to dry; removing the medical tubing from the mandrel after the solvent has dried; and subjecting the medical tubing to a sterilization process using ethylene oxide with in-chamber aeration.

Embodiments of the product may include one or more of the following features. In some embodiments, the solvent is cyclohexanone. In some embodiments, applying solvent where the turns of the medical tubing contact each other comprises: applying solvent at multiple points between each pair of adjacent turns of the medical tubing.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Medical tubing is commonly used in medical applications for transporting fluids such as saline solutions, medicinal solutions, and the like. But conventional medical tubing can be unwieldy. Lengths of medical tubing may, for example, snag on obstacles, trip or be stepped on by medical personnel, and the like. These hazards may be life-threatening for patients. In emergency medical situation such as those encountered by emergency medical technicians and firefighters, these hazards are only exacerbated.

Embodiments of the disclosed technology provide medical devices that include sterilized coiled medical tubing having turns that are attached yet separate easily, and methods of fabricating these medical devices. According to the disclosed technology, a length of medical tubing may be helically wound on a mandrel, and drops of solvent may be applied at points where adjacent turns of the medical tubing meet. After the solvent dries, the medical tubing may be removed from the mandrel, equipped with connections such as luer locks, clamps, and the like, and packaged. The packaged medical device may be sterilized. Certain sterilization processes may cause the medical tubing, and the attachments of adjacent turns of the medical tubing, to relax.

The resulting product features a helical coil of medical tubing having turns that adhere to one another, yet are easy to separate. Accordingly, a medical technician or firefighter can quickly and easily deploy a desired length of the medical tubing, while the remainder of the medical tubing remains coiled, with the adjacent turns still attached to each other. Furthermore, the deployed length of medical tubing retains its helical form, like a spring stretching only as far as needed. This feature greatly reduces the chance that the medical tubing will snag an obstacle, or be stepped on by medical personnel.

Figure 1:
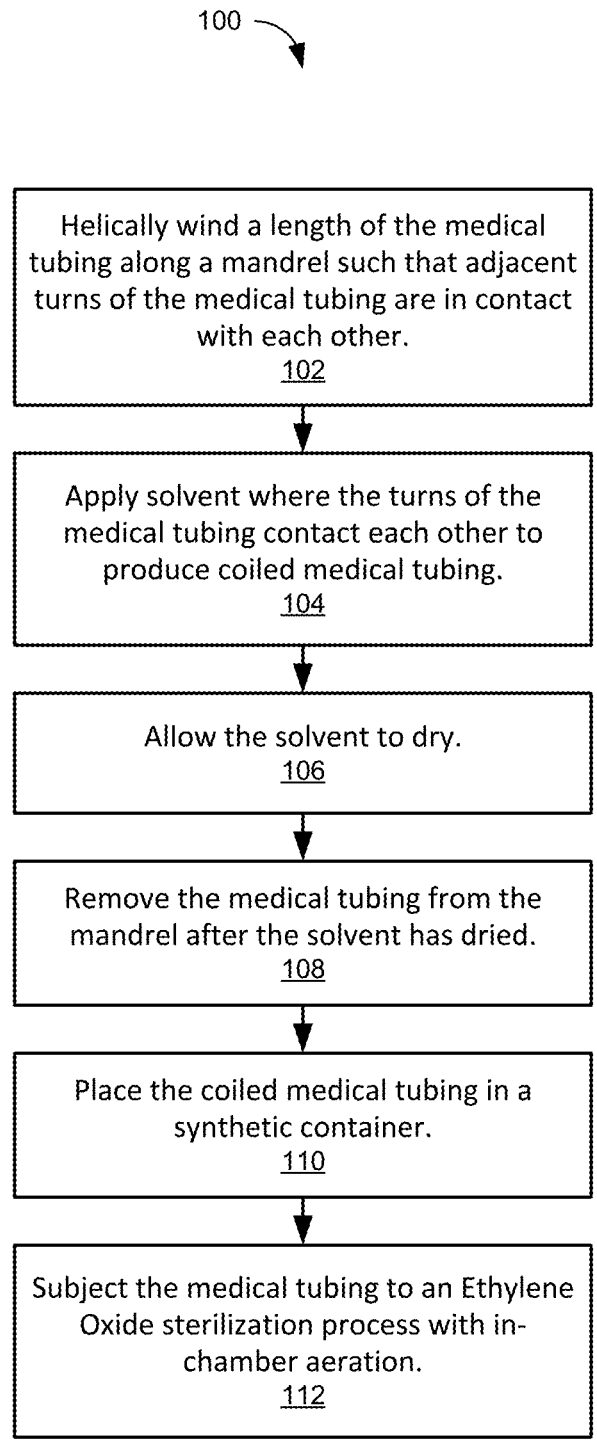
FIG. 1 illustrates a process for forming the sterilized, coiled medical tubing, and sterilized medical devices employing that tubing, according to some embodiments of the disclosed technology.

FIG. 1 illustrates a process 100 for forming the sterilized, coiled medical tubing, and sterilized medical devices employing that tubing, according to some embodiments of the disclosed technology. Referring to FIG. 1, the process 100 includes helically winding a length of the medical tubing along a mandrel such that adjacent turns of the medical tubing are in contact with each other, at 102. In some embodiments, the tubing is non-di(2-ethylhexyl) phthalate (DEHP) polyvinyl chloride (PVC) or DEHP-free PVC. However, other suitable materials may be used. Tubing of any length, inner diameter, and outer diameter may be used.

Figure 2:
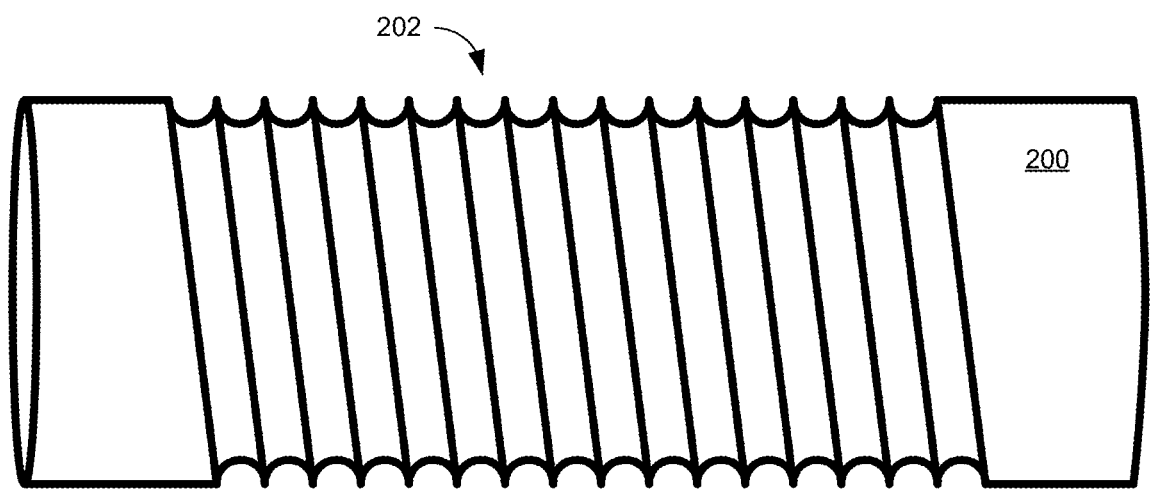
FIG. 2 illustrates a mandrel according to some embodiments of the disclosed technology.

FIG. 2 illustrates a mandrel 200 according to some embodiments of the disclosed technology. In some embodiments, the mandrel 200 is formed of polyoxymethylene. However, any suitable material may be used to form the mandrel 200. In some embodiments, the tubing may be helically loaded onto the mandrel with a manual winding or automated winding system, which stops at a desired length of the tubing.

Figure 3:
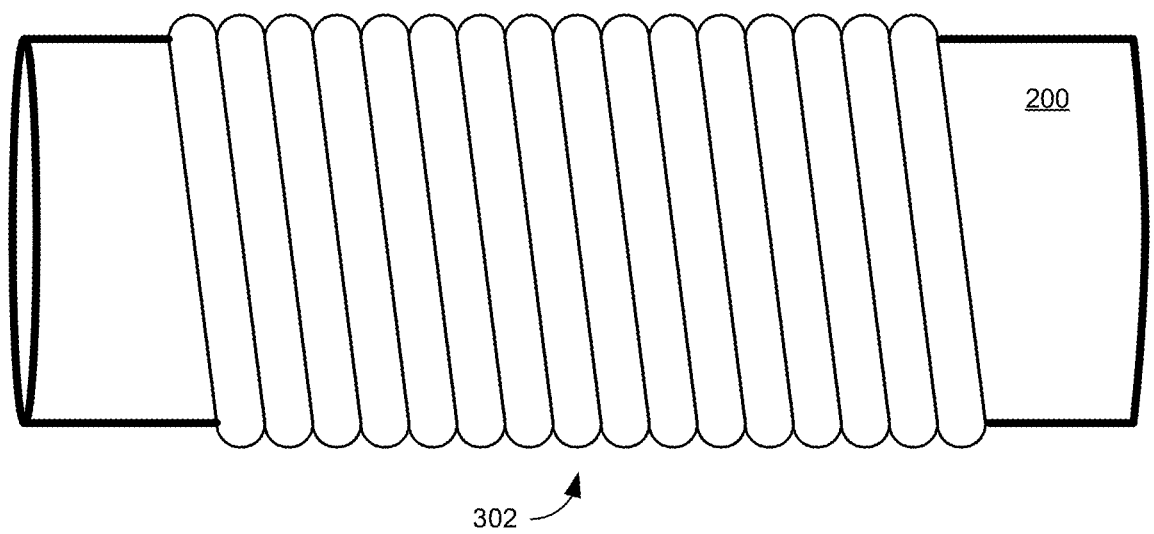
FIG. 3 illustrates a mandrel wound with medical tubing 302 according to some embodiments of the disclosed technology.

In some embodiments, the mandrel 200 may include helical grooves to receive the medical tubing, as shown at 202 in FIG. 2. Such embodiments may be useful for shorter lengths of medical tubing. In other embodiments, the mandrel 200 may be smooth. These embodiments may be useful for longer lengths of medical tubing. FIG. 3 illustrates a mandrel 200 wound with medical tubing 302 according to some embodiments of the disclosed technology.

Referring again to FIG. 1, the process 100 may include applying solvent where the turns of the medical tubing contact each other to produce coiled medical tubing, at 104. In some embodiments, drops of solvent are applied by a pin that has been dipped in the solvent. In some embodiments, the pin may be a metal pin. For example, the metal pin may be an Allen key or the like. In some embodiments, multiple pins may be used simultaneously. In some embodiments, the solvent may be applied by a air-powered fluid dispenser through appropriate hollow-needle dispensing pins sized to allow application of a precise, functional, drop of solvent. In some embodiments, the solvent is cyclohexanone.

Figure 4:
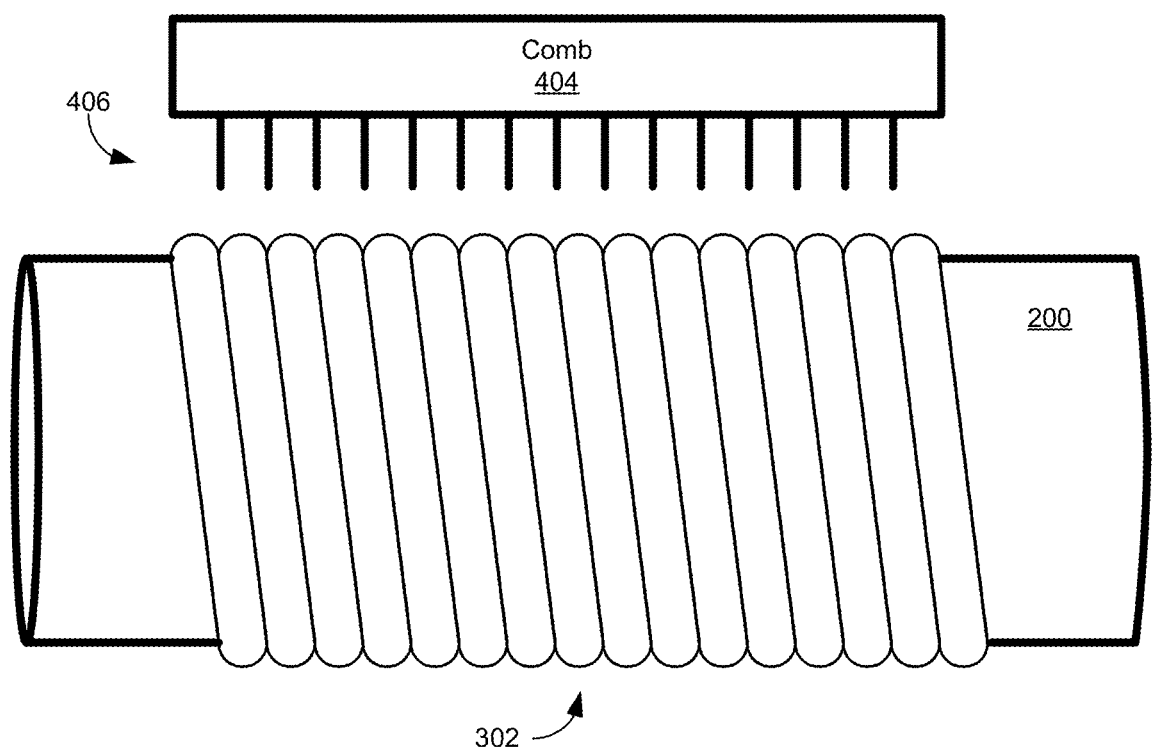
FIG. 4 illustrates a system for applying the solvent according to some embodiments of the disclosed technology.

FIG. 4 illustrates a system for applying the solvent according to some embodiments of the disclosed technology. Referring to FIG. 4, a comb 404 includes multiple pins 406. The pins 406 may have the same spacing as the turns of medical tubing 302. The comb 404 may be dipped into a bath of solvent such that the solvent adheres to the pins 406.

Figure 5:
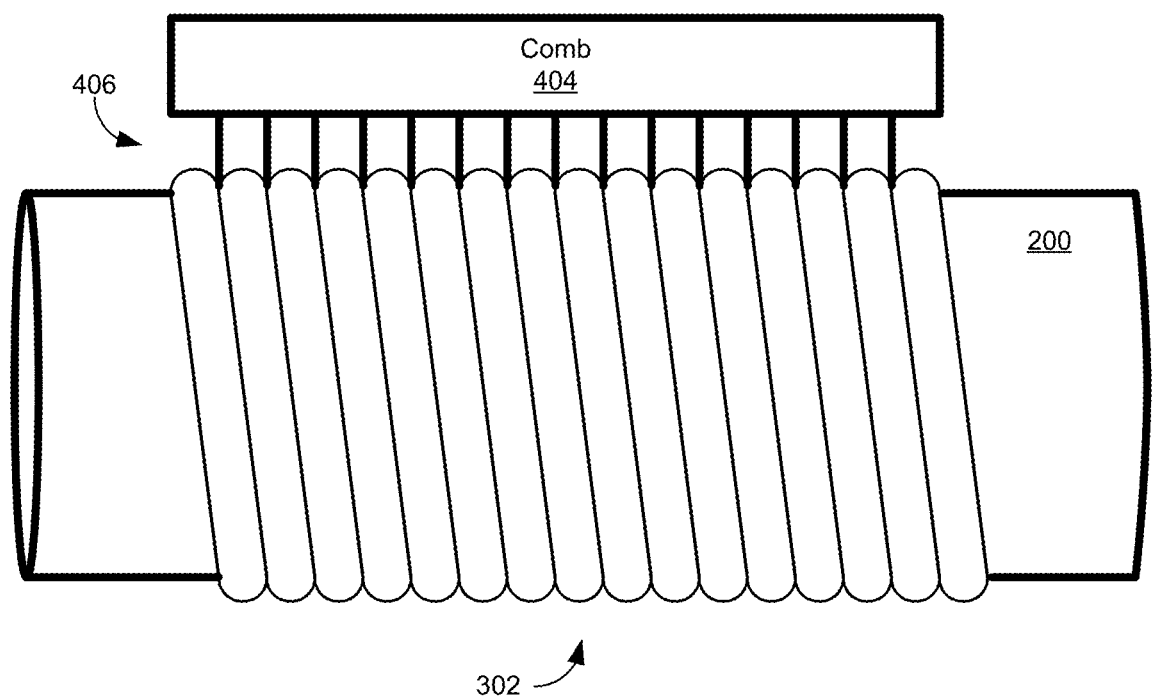
FIG. 5 illustrates the application of solvent to the tubing according to some embodiments of the disclosed technology.

FIG. 5 illustrates application of the solvent to the tubing 302 according to some embodiments of the disclosed technology. After applying the solvent to the pins 406, the comb may be moved towards the mandrel 200 such that the pins 406 dispose solvent between adjacent turns of the tubing 302. After disposing solvent upon the tubing 302, the comb 404 may be moved away from the mandrel 200 such that the pins 406 no longer contact the medical tubing 302.

In some embodiments, the solvent may be applied at multiple points between each pair of adjacent turns of the medical tubing. For example, after the initial application of the solvent to the medical tubing 302, the mandrel 200 may be rotated by a predetermined angle, followed by a second application of the solvent to the medical tubing 302. This process may be repeated as needed. For example, by rotating the mandrel 90 degrees between applications, adjacent turns of the medical tubing 302 may be attached at 4 points. Of course, other numbers of attachment points are contemplated.

Referring again to FIG. 1, the process 100 may include allowing the solvent to dry while the medical tubing 302 is on the mandrel 200, at 106. After the solvent has dried, the process 100 may include removing the medical tubing from the mandrel 200, at 108. In some embodiments, the mandrel 200 may be cooled slightly to facilitate removal of the medical tubing 302. For example, a fan may be used to blow cool air across the mandrel 200 and medical tubing 302.

Figure 6:
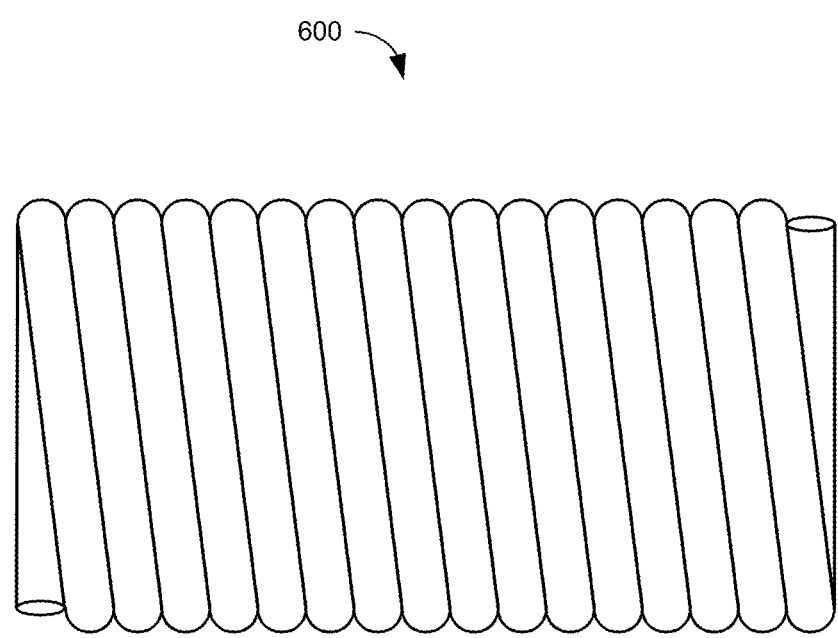
FIG. 6 illustrates the coiled medical tubing produced at this point in the process 100 according to some embodiments of the disclosed technology.

In embodiments where the mandrel 200 has helical grooves, the medical tubing 302 may be removed by rotating the mandrel 200 and the medical tubing 302 in opposite directions. In embodiments where the mandrel 200 is smooth, the medical tubing 302 may be removed by simply sliding the medical tubing 302 off one end of the mandrel. FIG. 6 illustrates the coiled medical tubing 600 produced at this point in the process 100 according to some embodiments of the disclosed technology. At this point, the turns of the coiled medical tubing 600 are tightly connected, and difficult to separate.

Referring again to FIG. 1, the process continues by placing the coiled medical tubing 600 in a synthetic container, at 110. In some embodiments, the container is made of flashspun high-density polyethylene fibers. One or more medical devices may be attached to the coiled medical tubing 600 prior to this packaging.

Figure 7:
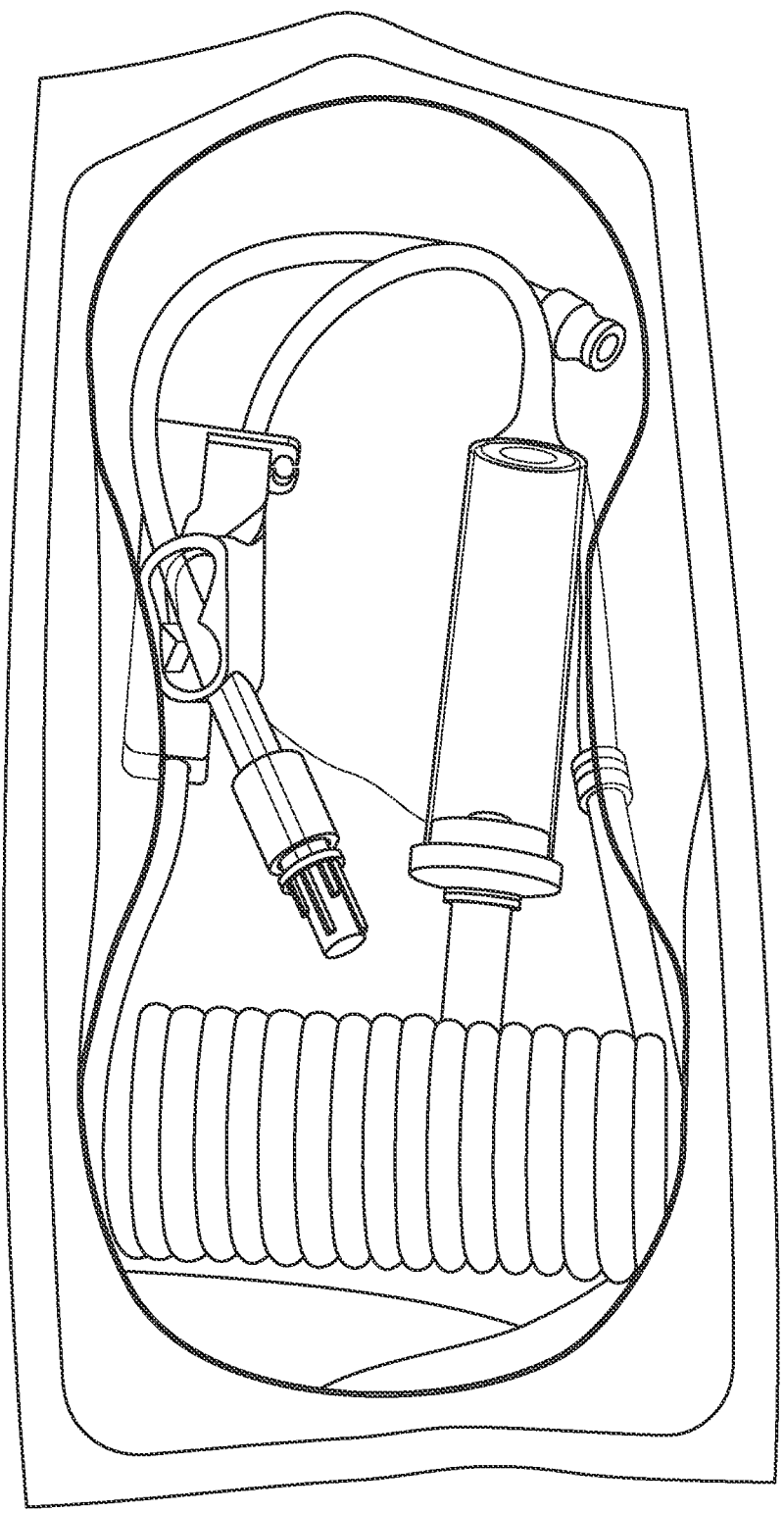
FIG. 7 is a photograph of coiled medical tubing with several medical devices attached according to some embodiments of the disclosed technology.

FIG. 7 is a photograph of coiled medical tubing with several medical devices attached according to some embodiments of the disclosed technology. Referring to FIG. 7, and beginning in the upper-right corner of the photographs, and proceeding counterclockwise, the devices include a 20 drop chamber, a short section of medical tubing, a roller clamp, coiled medical tubing according to some embodiments of the disclosed technology, a pre-pierced Y injection site, another short section of medical tubing, a needleless valve injection port, another short section of medical tubing, a pinch clamp, and a spin luer lock. The depicted medical device also includes breathers at open end ports. However, any suitable medical devices may be included.

Figure 8:
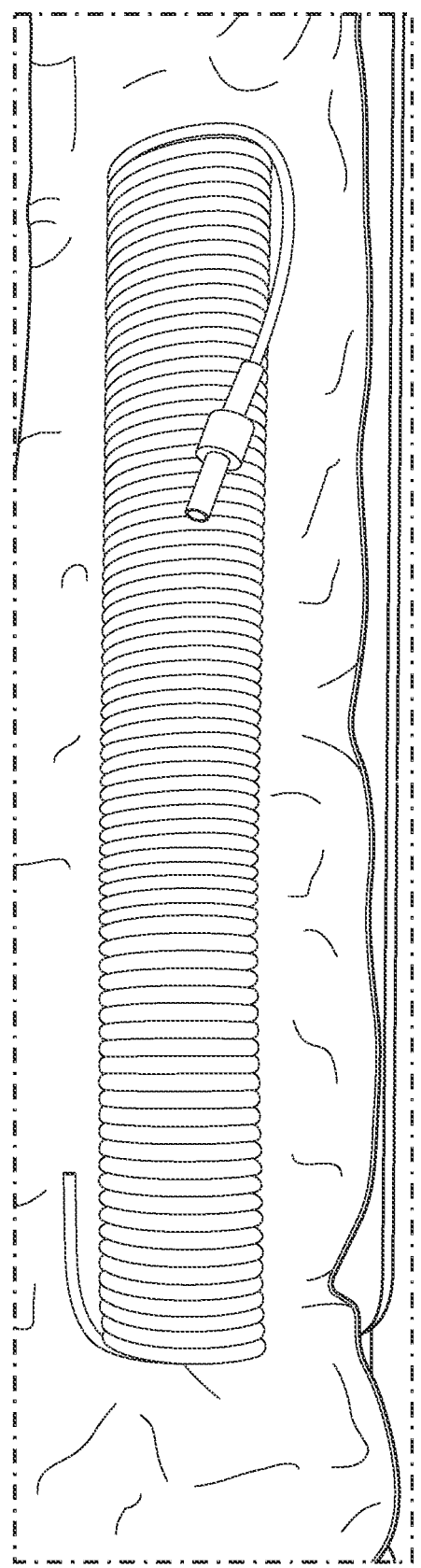
FIG. 8 is a photograph of packaged coiled medical tubing with spinlock connectors according to embodiments of the disclosed technology.

FIG. 8 is a photograph of packaged coiled medical tubing with spinlock connectors according to embodiments of the disclosed technology. Referring again to FIG. 1, after packaging, the coiled medical tubing 600, along with any attached medical devices, may be subjected to an sterilization process using ethylene oxide with in-chamber aeration, at 112. An example sterilization process is detailed the Appendix of this application.

Figure 9:
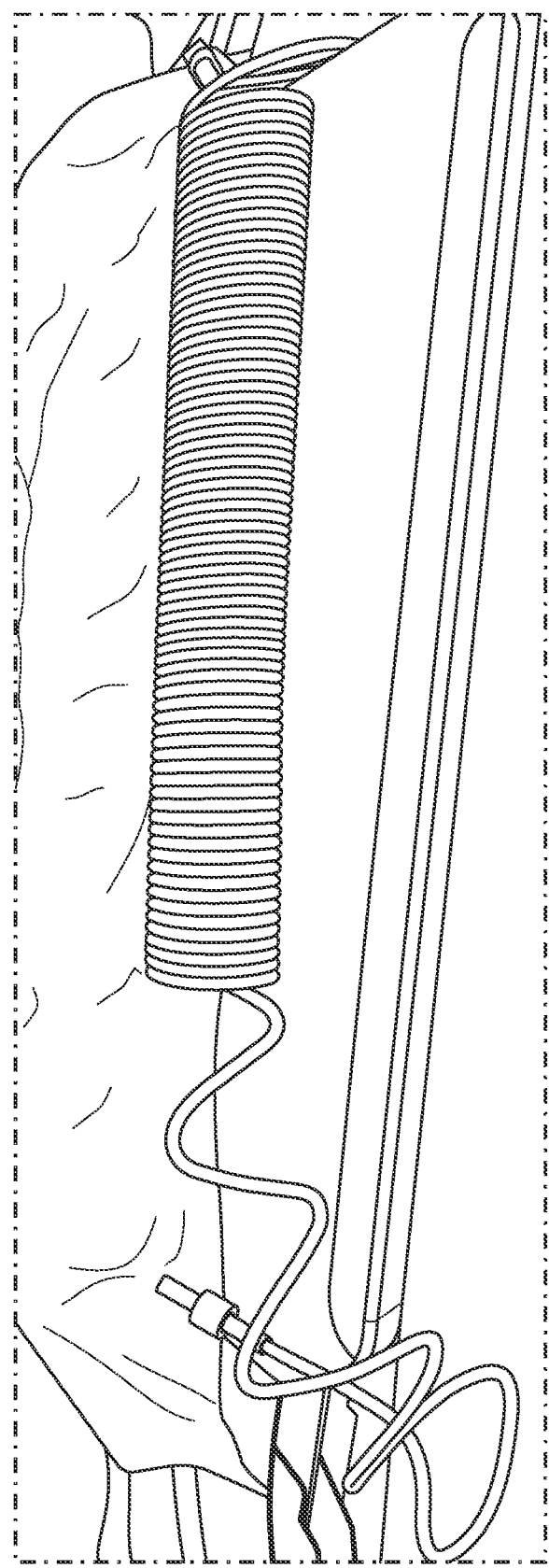
FIG. 9 is a photograph of coiled medical tubing with spinlock connectors after sterilization.

FIG. 9 is a photograph of coiled medical tubing with spinlock connectors after sterilization. At this point in the process, the turns of the coiled medical tubing 600 are still connected to each other, but are easy to separate, such that a desired length of the coiled medical tubing 600 may be deployed, while leaving the remaining turns connected as a single unit, as depicted in FIG. 9.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

A person of ordinary skill in the art will recognize that they may make many changes to the details of the above-described memory device without departing from the underlying principles. Only the following claims, however, define the scope of the memory device.

What is claimed is:

1. A process for producing a sterilized medical tubing coil, comprising:
   helically winding a length of medical tubing along a mandrel such that adjacent turns of the medical tubing are in contact with each other;
   applying solvent where the turns of the medical tubing contact each other to produce coiled medical tubing by:
      dipping a comb comprising a plurality of parallel pins into a container of the solvent such that the solvent adheres to the pins, wherein the parallel pins have the same spacing as adjacent turns of the medical tubing,
      disposing each of the parallel pins between respective turns of the medical tubing where the turns of the medical tubing contact each other, and
      removing the parallel pins from the turns of the medical tubing;
   allowing the solvent to dry such that the turns of the coiled medical tubing are connected to each other, but are separable;
   removing the medical tubing from the mandrel after the solvent has dried; and
   subjecting the medical tubing to a sterilization process using ethylene oxide with in-chamber aeration.

2. The process of claim 1, wherein:
   the solvent is cyclohexanone.

3. The process of claim 1, wherein:
   wherein the mandrel is formed of polyoxymethylene.

4. The process of claim 1, wherein:
   the tubing is non-DEHP PVC or DEHP-free PVC.

5. The process of claim 1, wherein:
   the parallel pins are metal.

6. The process of claim 1, further comprising:
   cooling the mandrel before removing the medical tubing from the mandrel.

7. The process of claim 1, wherein:
   a surface of the mandrel contacted by the turns of the medical tubing is smooth.

8. The process of claim 1, wherein:
   a surface of the mandrel contacted by the turns of the medical tubing has a helical groove to receive the medical tubing.

9. The process of claim 8, wherein removing the medical tubing from the mandrel comprises:
   rotating the mandrel and the medical tubing in opposite directions.

10. The process of claim 1, further comprising:
    placing the coiled medical tubing in a synthetic container after removing the coiled medical tubing from the mandrel, and prior to subjecting the coiled medical tubing to the ethylene oxide sterilization process with in-chamber aeration.

11. The process of claim 10, wherein:
    the synthetic container is made of flashspun high-density polyethylene fibers.

12. An apparatus for producing a medical tubing coil, comprising:
    a mandrel configured to helically wind a length of the medical tubing along the mandrel such that adjacent turns of the medical tubing are in contact with each other; and
    a comb comprising a plurality of parallel pins configured to apply solvent where the turns of the medical tubing contact each other to produce coiled medical tubing, wherein the parallel pins have the same spacing as adjacent turns of the medical tubing;
    wherein the solvent is allowed to dry before removing the medical tubing from the mandrel such that the turns of the coiled medical tubing are connected to each other, but are separable; and
    wherein the coiled medical tubing is subjected to a sterilization process using ethylene oxide with in-chamber aeration.

13. The apparatus of claim 12, wherein:
    the solvent is cyclohexanone.

14. The apparatus of claim 12, wherein:
    the comb is further configured to apply the solvent at multiple points between each pair of adjacent turns of the medical tubing.

* * * * *

UNITED STATES PATENT AND TRADEMARK OFFICE
CERTIFICATE OF CORRECTION

| | | |
|---|---|---|
| PATENT NO. | : 11,779,748 B2 | |
| APPLICATION NO. | : 17/037387 | |
| DATED | : October 10, 2023 | |
| INVENTOR(S) | : Knight | |

It is certified that error appears in the above-identified patent and that said Letters Patent is hereby corrected as shown below:

On the Title Page

Column 2, in "Assistant Examiner", Line 1, delete "Brad" and insert -- Brady --, therefor.

In the Specification

In Column 5, Line 3, delete "an" and insert -- a --, therefor.

In the Claims

In Column 6, Claim 3, Line 8, before "the", delete "wherein".

Signed and Sealed this
Second Day of January, 2024

Katherine Kelly Vidal
*Director of the United States Patent and Trademark Office*